United States Patent [19]

O'Malley et al.

[11] Patent Number: 5,834,213
[45] Date of Patent: Nov. 10, 1998

[54] SCREENING SYSTEM AND ASSAY FOR IDENTIFYING COMPOUNDS THAT REGULATE STEROID AND ORPHAN RECEPTORS MEDIATION OF DNA TRANSCRIPTION

[75] Inventors: Bert W. O'Malley; Orla M. Conneely; Ronan F. Power, all of Houston, Tex.

[73] Assignee: Baylor College of Medicine, Houston, Tex.

[21] Appl. No.: 225,071

[22] Filed: Oct. 1, 1993

Related U.S. Application Data

[62] Division of Ser. No. 694,585, May 2, 1991, abandoned.

[51] Int. Cl.[6] .............................. C12Q 1/00; G01N 33/53; C12P 21/06
[52] U.S. Cl. ........................... 435/7.8; 435/7.2; 435/69.1; 435/320.1; 435/240.1; 536/23.1
[58] Field of Search ............................ 43/7.1, 7.2, 320.1, 43/240.1, 69.1, 69.4, 69.7; 536/23.51, 23.1

[56] References Cited

U.S. PATENT DOCUMENTS 4,981,784  1/1991  Evans et al. ..................... 435/6

OTHER PUBLICATIONS

Prager et al. 1990 Clin Res 38(2) :410 A.
Castrillo et al 1989 Science 243 :814–817.
Nyborg et al 1986 J. Biol Chem 261(13): 5685–5688.
Denner et al. 1990. Science 250 :1740–1743.
Kandel et al 1981 Principles of Neural Science, Elsevier/North, Holland, pp. 116–117, 629, 630.
Cooper et al. 1978 The Biochemical Basis of Neuropharmacology 3rd Ed. Oxford Univ. Press, New York, pp. 97, 218, 180–181, 292–293.

*Primary Examiner*—Vasu S. Jagannathan
*Assistant Examiner*—Karan Cochrane Carlson
*Attorney, Agent, or Firm*—Fulbright & Jaworski L.L.P.

[57] ABSTRACT

A tissue culture screening system to monitor a transcriptional response treated by a chemical signal interacting with a plasma membrane receptor is provided. The tissue culture screening system includes a cell line containing a membrane receptor, a target gene and a specific receptor selected from the group consisting of a steroid receptor, a vitamin receptor and an orphan receptor. The specific receptor regulates transcription of the target gene. Any of the target gene membrane receptor or specific receptor can be introduced into the cell by an expression vector. In addition to the screening system there is also provided assays for identifying test compounds and chemical signals that regulate transcription or are potential agonist or antagonist neurotransmitters or which regulate indirectly by a membrane receptor binding or regulate transcription in the absence of a steroid, vitamin or orphan ligand. There is further provided kits for the assays.

6 Claims, 12 Drawing Sheets

SCREENING SYSTEM AND ASSAY FOR IDENTIFYING COMPOUNDS THAT REGULATE STEROID AND ORPHAN RECEPTORS MEDIATION OF DNA TRANSCRIPTION

This is a divisional of application Ser. No. 07/694,585, filed May 2, 1991, now abandoned.

This invention was partially supported by grants from the United States Government. The government has certain rights in the invention.

FIELD OF THE INVENTION

The present invention relates generally to a system for detecting compounds which interact with the steroid, vitamin or orphan receptor dependent pathway of gene activation. The system can be used in an assay to detect the coupling of the activation of membrane receptors to gene expression and to monitor compounds which directly or indirectly affect transcription through the receptor dependent pathway of gene activation.

BACKGROUND OF THE INVENTION

Steroid hormones are potent modulators of transcriptional events that together regulate the complex processes associated with differentiation homeostasis and development. The mechanism of action of these molecules is related in that the effector molecule binds to a specific intracellular receptor. This binding alters the structure of the receptor, thus increasing its affinity for specific recognition sites within the regulatory region of target genes. In this way, the steroid directs a program of events that leads to a change in cell phenotype.

Steroid hormones, thyroid hormones and certain vitamins can regulate cellular differentiation morphogenesis and homeostasis by binding to specific intracellular receptor proteins. Ligand activated receptor complexes are capable of activating or repressing transcription of a specific set of target genes. Thus, the receptor proteins are capable of reprogramming cellular function at the genomic level in response to hormonal or vitamin signals.

The isolation and sequencing of the DNA clones encoding these receptor proteins provided evidence that the receptors comprise a family of closely related genes. Additional members of this family have been identified on the basis of amino acid sequence homologies appearing in three regions of the proteins. The $C_1$ region contains a highly conserved DNA binding domain, while the consensus regions $C_2$ and $C_3$ are located in the ligand binding domain of the receptors. Approximately 20 new members of this gene family have been identified. The presence of consensus regions $C_2$ and $C_3$ has lead to speculation that the new members of this family are also ligand activated transcription factors. However, since no ligand has been identified which directly activates any of the new members of this family, they are "orphan receptors" in search of a ligand. A limited number of compounds have been identified which can activate the specific orphan receptors indirectly. However, the mechanism by which these compounds activate the respective orphan receptors and the physiological relevance of these activators is unclear.

For several years it has been accepted dogma that steroid receptors can be activated only by their specific cognate ligands. Further it has been thought that chemical signals which bind to membrane receptors exert their biological effects through pathways which are separate and independent of the steroid receptor pathways.

The present invention shows that there is cross-talk between membrane receptors and steroid receptors. Further, there is provided a new system for detecting the ability of a wide range of compounds to bind membrane receptors, alter intracellular phosphorylation and to activate transcription by steroid, vitamin, orphan and chimeric receptors. This system and the method of using the system in an assay demonstrate that the binding to membrane receptors is coupled to a phosphorylation event which activates steroid receptors and regulates transcription.

SUMMARY OF THE INVENTION

An object of the present invention is development of a tissue culture screening system to monitor transcriptional responses.

An additional object of the present invention is the provision of a tissue culture screening system with a chimeric receptor for measuring transcriptional responses.

A further object of the present invention is an assay for identifying compounds or chemical signals which regulate transcription.

Another object of the present invention is an assay which measures agonists and antagonists of neurotransmitters which regulate cellular target genes.

A further object of the present invention is an assay for measuring compounds which activate a membrane receptor and regulate gene activation or repression.

An additional object of the present invention is a kit containing a tissue culture screening system for monitoring transcriptional responses.

Thus in accomplishing the foregoing objects there is provided, in accordance with one aspect of the present invention, a tissue culture screening system to monitor a transcriptional response triggered by a chemical signal interacting with a plasma membrane receptor, comprising a cell line containing the membrane receptor, a target gene and a specific receptor selected from group consisting of a steroid receptor, a vitamin receptor, an orphan receptor and a chimeric receptor, wherein said specific receptor regulates transcription of said target gene.

In more particular embodiments of this invention any one or all of the membrane receptor, the target gene and the specific receptor can all be incorporated into the tissue culture system through expression plasmids.

Additional aspects of the present invention include the use of the tissue culture screening system: (1) to measure compounds which regulate the biological activity of steroid, vitamin or orphan receptors; (2) to monitor transcriptional responses from compounds interacting with the plasma membrane receptor; (3) to identify compounds which couple the activation of membrane receptors to gene expression; and (4) to identify non-ligand compounds which trigger steroid, vitamin and orphan receptor regulation of gene expression.

An additional embodiment of the present invention is a method of making the tissue culture screening system comprising the steps of growing the tissue culture cell line until cell growth has reached approximately 50% confluence and transfecting the tissue culture with an appropriate expression plasmid for any or all of membrane receptor, target gene and specific receptor.

Other and further objects, features and advantages will be apparent from the following description of the presently preferred embodiments of the invention, given for the purpose of disclosure when taken in conjunction with the accompanying drawings.

Figure 1:
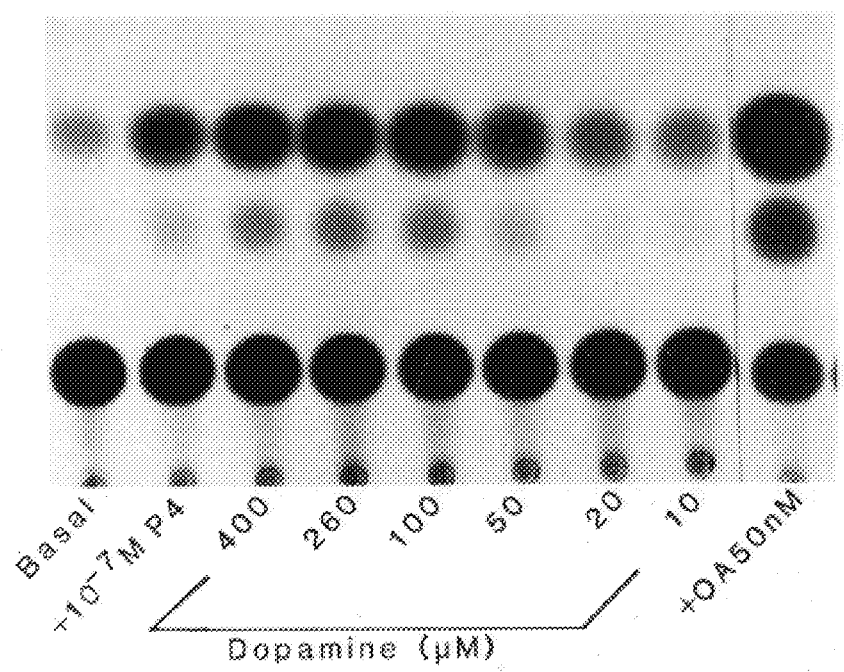
FIG. 1 shows the activation of the steroid receptor for progesterone (PR) by progesterone, dopamine and okadaic acid.

The drawings are not necessarily to scale. Certain features of the invention may be exaggerated in scale or shown in schematic form in the interest of clarity and conciseness.

DETAILED DESCRIPTION

It is readily apparent to one skilled in the art that various substitutions and modifications may be made to the invention disclosed herein without departing from the scope and spirit of the invention.

The term "orphan receptor" as used herein refers to a family of approximately 20 receptors which have been identified by amino acid sequence homologies. The orphan receptor has an amino acid sequence which is highly conserved in the DNA binding domain and has consensus regions located in the ligand binding domain of the receptor. They are called orphan receptors because no ligand has been identified which directly activates any of the members of this family. An example of an orphan receptor is the chicken ovalbumin upstream promoter transcription factor (COUP-TF).

The term "chimera" as used herein means a strand of DNA formed by the fusion of the genetic sequence of two different receptors. Steroid receptors are composed of both a DNA binding domain and a hormone binding domain. In the chimeric receptor the DNA binding domain is composed of the genetic code from one receptor and the hormone binding domain is composed of a genetic code from another receptor. These two domains are fused to form a chimeric receptor. The domains can be from different species or from different receptors within the same species.

The term "transfection" as used herein refers to the transformation of a cell with DNA from a virus or expression plasmid. In this mechanism, there is transfer of genetic material, whereby DNA extracted from the donor is able to induce permanent genetic change in the recipient with respect to those characteristics in which the two strains differ.

The term "expression plasmid" or "expression vector" as used herein refers to a cloning vehicle (viral or plasmid) which has been specifically modified to permit insertion of foreign DNA into a cell. They normally contain all the appropriate signals necessary for transcription of the inserted DNA in a suitable whole cell.

The term "tissue culture screening system" as used herein refers to a system which can be used to test for compounds or chemical signals which regulate the transcriptional response. The tissue culture screening system comprises a cell line containing a membrane receptor, a target gene and a specific receptor, wherein the specific receptor regulates transcription of the target gene.

The term "specific receptor" as used herein refers to a receptor selected from the group consisting of a steroid receptor, a vitamin receptor, an orphan receptor and a chimeric receptor.

The term "reporter gene" as used herein refers to any of the variety of genes which produce a protein when transcription is activated by a test compound or chemical signal. This protein is measured to determine the effect on transcription.

The term "target gene" as used herein refers to a gene whose transcription is responsive to a specific receptor. The target gene is usually composed of a receptor response enhancer DNA element located upstream of a basal promoter which is fused to a reporter gene.

One embodiment of the present invention is a tissue culture screening system to monitor a transcriptional response triggered by a chemical signal interacting with a plasma membrane receptor.

In specific embodiments of the present invention: (1) the membrane receptor can be incorporated into the system by transfecting the cell line with an expression vector or plasmid containing a cDNA or genomic DNA sequence encoding the membrane receptor; or (2) the target gene can be incorporated into the system by transfecting the cell line with an expression plasmid containing a receptor-responsive target gene; or (3) the specific receptor regulating transcription of the target gene can be incorporated into the system by transfecting the cell line with an expression plasmid containing a cDNA or genomic DNA sequence encoding the specific receptor; or (4) any combination of the membrane receptor, target gene or specific receptor can be simultaneously incorporated into the system by transfecting appropriate expression plasmids.

Additional embodiments of the present invention include a tissue culture screening system for: (1) the identification of compounds or chemical signals which regulate the biological activity of a steroid receptor, a thyroid receptor, a vitamin receptor or an orphan receptor; or (2) testing the coupling of the activation of membrane receptors with gene expression; or (3) monitoring a transcriptional response triggered by a chemical signal interacting with a plasma membrane receptor. The preferred embodiments of these systems are each comprised of a first expression plasmid including a cDNA encoding the receptor whose biological activity is being tested; a second expression plasmid, including a receptor responsive target gene, wherein the target gene comprises a receptor responsive enhancer DNA element located upstream of a basal promoter which in turn is fused to a reporter gene; and a transfectable tissue culture cell line wherein the tissue culture cell line is transfected with the first and second expression plasmids.

In the systems described herein the tissue culture cell line can be devoid of the receptor whose biological activity is being tested. In this case the missing receptor is added to the cell line by transfection of a plasmid carrying the cDNA for the missing receptor or a chimera for the deficient receptor.

The receptor responsive enhancer DNA element is selected from the responsive elements corresponding to the specific receptor used in the system.

The basal promoter consists of a minimal promoter sequence that contains a 'TATA' element capable of binding RNA polymerase II and is selected from any of the commonly used elements. For example, thymidine kinase promoter, ovalbumin promoter and MMTV LTR.

The reporter gene can be selected from any of the variety of genes in which the protein product is easily assayed or detected. One skilled in the art readily recognizes that the protein can be easily assayed by calorimetric, fluorescent; immunochemical, chemical or radiochemical methods. Further the reporter gene can be a chimera. Examples of various reporter genes which can be used include the bacterial enzyme chloramphenicol acetyl transferase (CAT), β-galactosidase, alkaline phosphatase, luciferase, peptide hormones, growth factors and chimeric proteins. In the preferred embodiment genes producing non-native proteins are used. For example, CAT is used in mammalian systems because it is not a normally occurring enzyme in mammalian cells and is easy to assay. Thus, the receptor dependent activation of CAT in tissue culture cells was used to identify compounds which directly or indirectly interact with receptor to activate transcription of the target gene.

The compounds or chemical signals which can activate the steroid, vitamin, orphan or chimeric receptors in the above assays and can do so either by direct ligand binding to the receptor (for example, progesterone, estrogen and androgens) or by an indirect pathway such as simulation of receptor phosphorylation or binding to a membrane receptor.

Another specific embodiment of the present invention is a tissue culture screening system wherein at least one expression plasmid containing a cDNA encoding a chimeric specific receptor wherein the hormone binding domain of the specific receptor is selected from the group consisting of a vitamin receptor, a hormone receptor and an orphan receptor and a DNA binding domain is from a different receptor. This is essentially useful if the cell line is not devoid of the specific receptor being tested or when trying to identify compounds which interact with orphan receptors.

In all of the tissue culture screening systems described herein the cell line can be any of the commonly used cell lines which are transfectable. Examples of these cell lines used in the present invention include: Chinese hamster ovary, vaginal epithelial carcinoma, HeLa, $C_6$ glioma, anterior pituitary ATT20, human breast carcinoma, $T_{47}D$, MCF-7 and monkey kidney CV-1 cells.

A further enhancement of the transfected cell lines is to create a cell line which is stably transfected by introducing a plasmid containing a selectable marker gene. One skilled in the art readily recognizes that a variety of selectable marker genes can be used to create a stable transfected cell line. In the present invention it is found that the use of Neomycin reistance cassette, dihydrofolate reductase and adenosine deaminase are successful in making a stable transfected cell line.

One skilled in the art will readily recognize that the cell line can be devoid of the specific receptor which is being tested or can indeed have the specific receptors being tested. In the latter case, one skilled in the art will readily recognize that the reporter gene has to be carefully chosen and that the use of chimeric receptors would be very useful in detecting the effect of the compound or chemical signal when the receptor is normally present in the cell.

A variety of specific receptors have been used in the present invention. They can be either steroid, vitamin, thyroid or orphan receptors. Examples of these receptors are the COUP-TF, Vitamin D (VDR), retinoic acid (RAR), progesterone (PR), androgen (AR), TR2 (testes receptor 2), thyroid receptor (TR) and estrogen related receptors (ERR1 and ERR2). In addition, as discussed above, any of the receptors can also be chimeric receptors to help in the assay as well as to help identify responsive elements for receptors.

In making the chimeric receptor, the chimera usually comprises a DNA binding domain of one receptor and a hormone binding domain of a second receptor. In the present invention it is found that the DNA binding domain is usually selected from a group of receptors whose specific enhancer DNA elements have been identified, e.g., PR, ER, TR, GR, VDR, and RAR. Further, the DNA bnding domains of the yeast transcription factor Gal4 and bacterial transcription factor LexA can also be used.

A further embodiment of the present invention is a method of making the tissue culture screening system comprising the steps of growing the tissue culture cell line until cell growth has reached approximately 50% confluence; and transfecting the tissue culture with the appropriate expression vector to make the test system. As described above, the plasmid can include a membrane receptor, a target gene, a steroid receptor, a vitamin receptor, an orphan receptor, and a chimeric receptor.

A further embodiment of the present invention is an assay for identifying a test compound or chemical signal that regulates transcription, comprising the steps of growing a tissue culture screening system in appropriate media, wherein the cell line of the tissue culture screening system contains a membrane receptor, a target gene and a specific receptor selected from the group consisting of a steroid receptor, a vitamin receptor, an orphan receptor or a chimeric receptor; adding the test compound or chemical signal to the media and measuring the amount of product produced by the target gene. One skilled in the art will readily recognize that the media chosen depends on the cell line chosen. The receptors and target genes can be added by either transient or stable transfection.

This assay can be used for testing a variety of characteristics of the test compounds or chemical signals. For example, the assay can be applied: (1) to test if the compound or chemical signal is potentially an agonist or antagonist of neurotransmitters which regulate cellular target genes; or (2) to test if the compounds or chemical signals potentially act indirectly by membrane receptor binding to regulate a steroid, vitamin or orphan receptor pathway of gene activation or repression; or (3) to test if the compound or chemical signal acts through the dopaminergic receptor, the α or β adrenergic receptor, cholinergic receptor, muscarinic receptor, nicotinic receptor and serotinergic receptor; or (4) to test if the compound or chemical signal potentially activates a specific receptor dependent gene regulatory pathway in the absence of the ligand for the specific receptor; or (5) to test whether the compound or chemical signal is a non-ligand antagonist that interferes with steroid, vitamin or orphan receptor dependent regulated gene activation. Thus, the assay described herein is applicable to test for a variety of effects on transcription and to monitor a transcriptional response after testing with compounds or chemical signals.

An additional embodiment of the present invention is a kit for measuring receptor dependent regulated transcription comprising the container having a stable transfected cell line wherein the cell line includes a membrane receptor, a target gene and a specific receptor selected from the group consisting of a steroid receptor, a vitamin receptor, an orphan receptor and a chimeric receptor.

The kit can also include a cell line in which at least one of the plasma membrane receptor, the target gene and the specific receptor, is included as an expression plasmid.

Additionally, the kits can include control compounds to test if the tissue culture screening system assay is working.

The following examples are offered by way of illustration and are not intended to limit the invention in any manner. The synthetic oligonucleotides described in the examples can include any of the substitutions discussed earlier.

EXAMPLE 1

Cell Culture and Transfection

CV-1 monkey kidney cells were obtained from the American Type Culture Collection (ATCC) and were maintained in Dulbecco's modified eagle medium—10% fetal bovine serum—100 μg of penicillin per ml—100 μg of streptomycin. per ml, in the presence of 5% $CO_2$ at 37° C. Cells were split 24 hr prior to transfection, seeded at $1\times10^6$ cells per 100 mm dish and allowed to attach as a monolayer in DMEM containing 10% fetal bovine serum for 4 h. After this period the plates were rinsed with Hanks buffered saline solution minus calcium minus magnesium and were fed with DMEM containing 1% Nutridoma-SR (Boehringer-Mannheim, Indianapolis, Ind.).

For transfection, appropriate expression plasmids (1–5 μg DNA) were used. In one example an expression plasmid containing the progesterone receptor and an expression plasmid containing the progesterone responsive enhancer DNA element located upstream of a thymidine kinase promoter which is fused to a CAT gene was used. The DNA was mixed with polybrene (50 μg) [S. Kawai and M. Nishizawa, Mol. Cell. Biol. 4, 1172 (1984)] and was incubated with the CV-1 cells in 10 ml of serum free media for 4 hr. Cells were then shocked with 25% glycerol for 45 s [M. A. Lopata, D. W. Cleveland, B. Sollner-Webb, Nucleic Acids Res. 12, 5705 (1984)], washed with Hanks buffered saline solution and cultured in DMEM containing 1% Nutridoma-SR and penicillin/streptomycin. Compounds isoproterenol, okadaic acid, quinperole, alpha-ergocryptine and 8-bromo-cyclic adenosine monophosphate were added 15 min after glycerol shock. Protein extracts from the cells were made and assayed for CAT activity 48 hr post-shock.

EXAMPLE 2

CAT Assay

The CAT activity assay is similar to that described in C. M. Gorman, L. F. Moffatt and R. M. Howard, Mol. Cell. Biol. 2, 1044 (1982). The assay is as follows:

In an assay tube add about 2.5 μl (0.25 μCi) $^{14}$C-chloramphenicol and cell lysate (about 10–100 μg protein), then bring the volume up to 30 μl with 0.25M TRIS, pH7.8. Next add 30 μl acetyl-CoA solution (4 mM or 3,22 mg/ml in 0.25M TRIS pH7.8) and mix thoroughly. Then incubate for about 5 h. to overnight in 30° C. water bath. After incubation, add 1 ml ethyl acetate to the assay tube and mix thoroughly. Centrifuge at 10,000 g for 3 minutes at room temperature. Remove the aqueous upper phase to a fresh tube and dry down the extract in a speedvac with heat for about 30 m. Add about 20 μl ethyl acetate to the extracted CMP and mix. Spot on TLC plate: Run with solvent (95% chloroform/5% methanol for 80% of plate). Air dry plates and place in contact with Kodak rapid X-ray film for 1–2 days. The developed film showed the spotted origin with the free chloramphenicol followed by 1 acetyl, 3 acetyl and 1,3 diacetylated forms. Cut out appropriate parts of TLC plates for scintillation counting. The % conversion is calculated as GPM converted/CPM converted+CPM unconverted.

EXAMPLE 3

Assay System to Detect Chemical Signals

As described above, 5 μg of each receptor expression plasmid was transfected together with 5 μg of cognate target plasmid (which differ by the inclusion of different receptor specific enhancer sequences) into CV-1 cells and incubated with the indicated concentrations of specific ligand, dopamine or okadaic acid.

Figure 2:
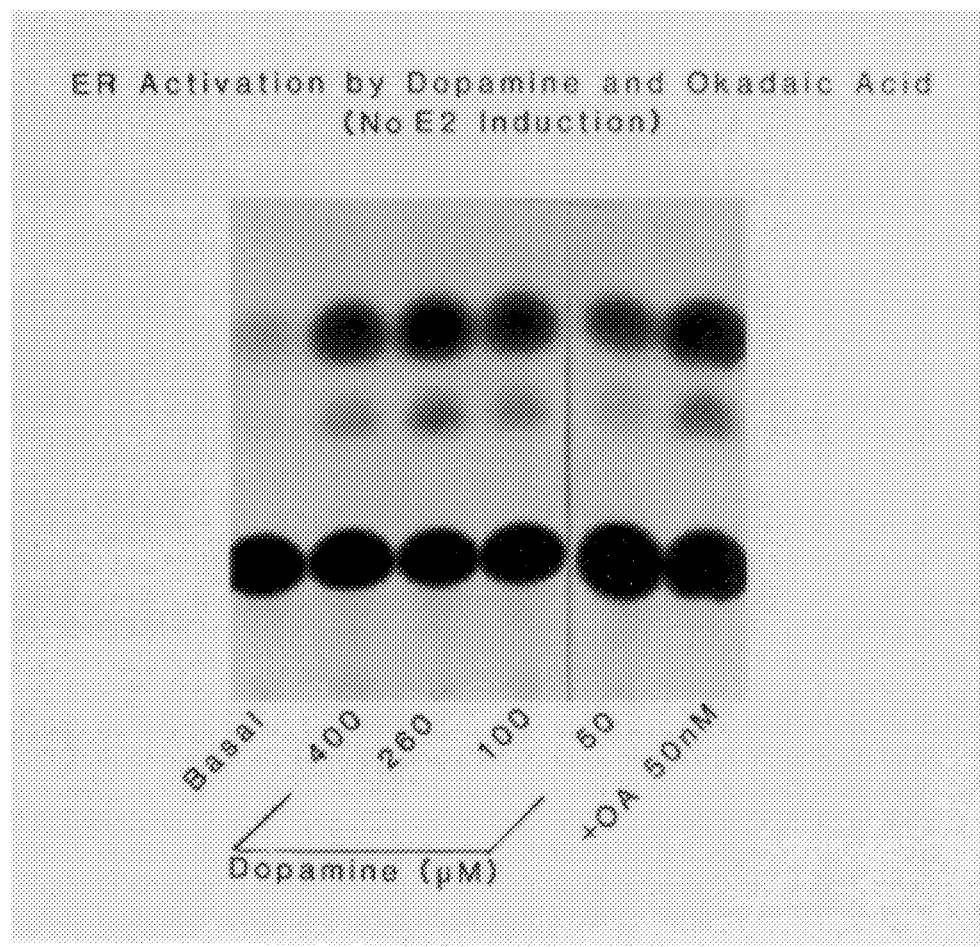
FIG. 2 shows the activation of estrogen (ER) receptor by dopamine and okadaic acid.
Figure 3:
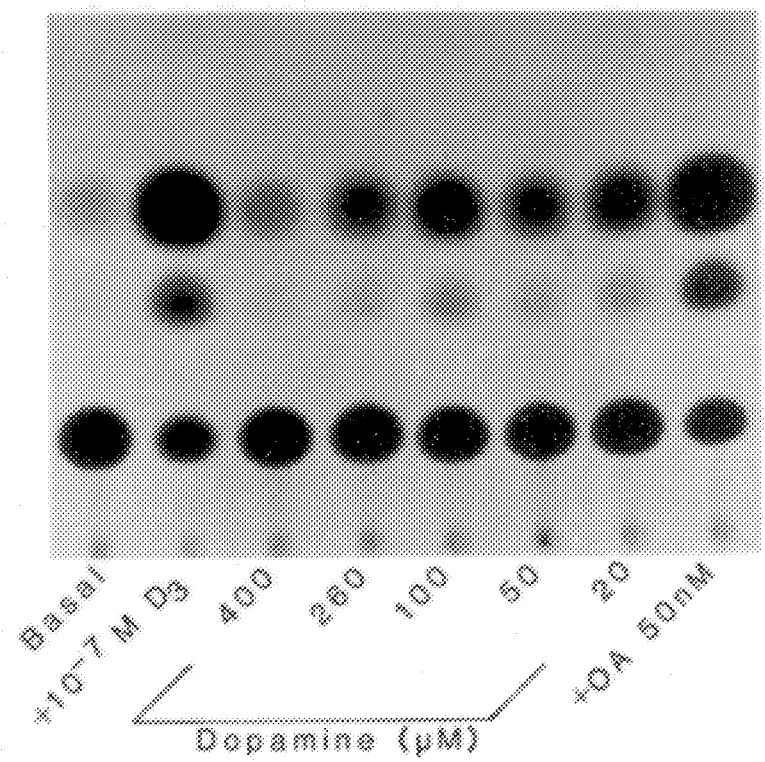
FIG. 3 shows the activation of the vitamin receptor for vitamin D (VDR) by vitamin $D_3$, dopamine and okadaic acid.
Figure 4:
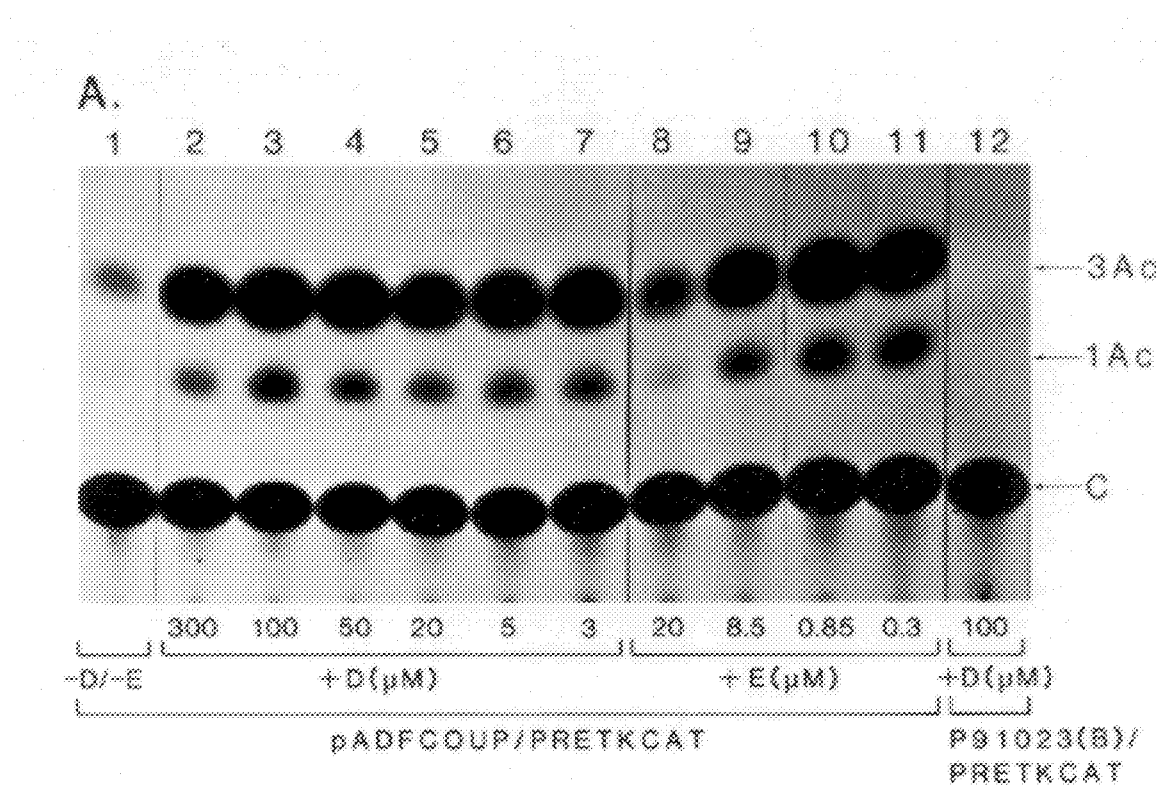
FIG. 4 shows the activation of the chicken ovalbumin upstream promoter transcription factor COUP-TF receptor by dopamine, okadaic acid and α-ergocryptine.

As seen in FIGS. 1–4, the receptors for progesterone (PR), estrogen (ER), Vitamin D (VDR) and the orphan receptor COUP-TF are activated by their cognate ligands (progesterone P-4, vitamin $D_3$), the phosphatase inhibitor okadaic acid and by physiological concentrations of dopamine. It can be seen that the progesterone receptor dependent target gene (PRETKCAT) is activated by progesterone, dopamine and okadaic acid (FIG. 1). The estrogen receptor dependent target gene (ERETKCAT) is activated by dopamine and okadaic acid (FIG. 2). The VDR dependent target gene (VDRETKCAT) is activated by vitamin $D_3$, dopamine and okadaic acid (FIG. 3). The COUP-TF dependent target gene is activated by dopamine and okadaic acid (FIG. 4).

Figure 9:
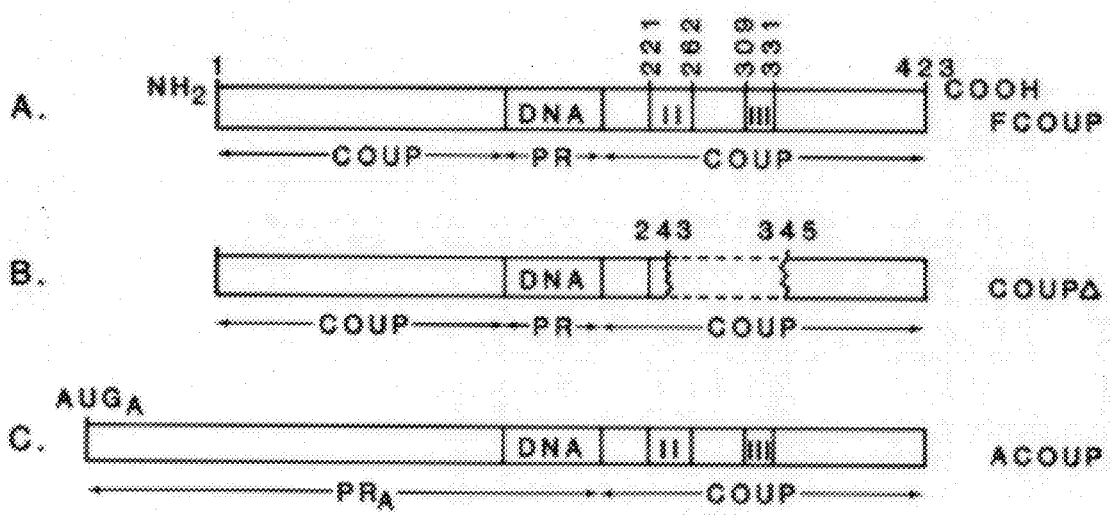
FIG. 9 shows the structure of the chimeric COUP-TF receptor. (A) The chimeric COUP-TF (FCOUP) with the $NH_2$ and COOH-terminal domains of human COUP-TF fused to the DNA binding domain of cPR. The boundaries of domains II and III, which are conserved among the steroid receptor family, are indicated by amino acid number. (B) The COOH-terminal deletion mutant of (A) (COUP Δ). (C) The $PR_A$-COUP chimera (ACOUP) with the $NH_2$ and DNA binding domains of cPR (A form) fused to the COOH-terminal domain of COUP-TF.

Since the COUP DNA enhancer element which directs COUP-TF dependent activation of a basal promoter is not known, the present invention employed a different strategy to assay for COUP-TF dependent gene activation. In order to provide a suitable target gene, a chimera was made as described herein. The cDNA fragment encoding the binding domain of COUP-TF was replaced with the progesterone receptor counterpart (FIG. 9). This "domain switch" strategy alters the enhancer DNA binding specificity of COUP-TF so that the orphan receptor now recognizes the progesterone receptor responsive target gene (PRETKCAT). The "domain switch" approach has two advantages: (1) it provides a suitable target gene to identify compounds which activate orphan receptors whose cognate enhancer DNA elements have not been identified and (2) it prevents competition from endogenous orphan receptors that may occur in CV-1 or alternative cell lines used in the assay.

EXAMPLE 4

Nuclear Receptor Activation by Dopamine

Figure 5:
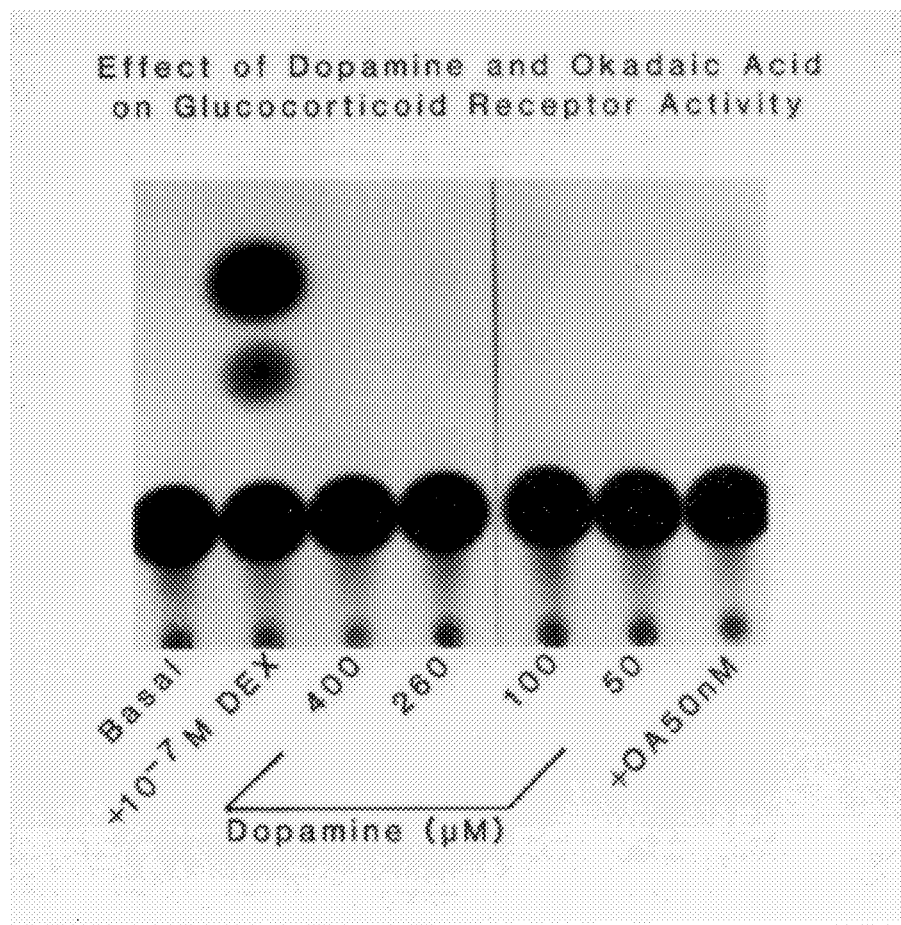
FIG. 5 shows that the nuclear receptor activation by dopamine is confined to a subgroup of the steroid/orphan receptor family and that the glucocorticoid receptor is activated by its cognate ligand, dexamethasone, but is not activated by dopamine.
Figure 6:
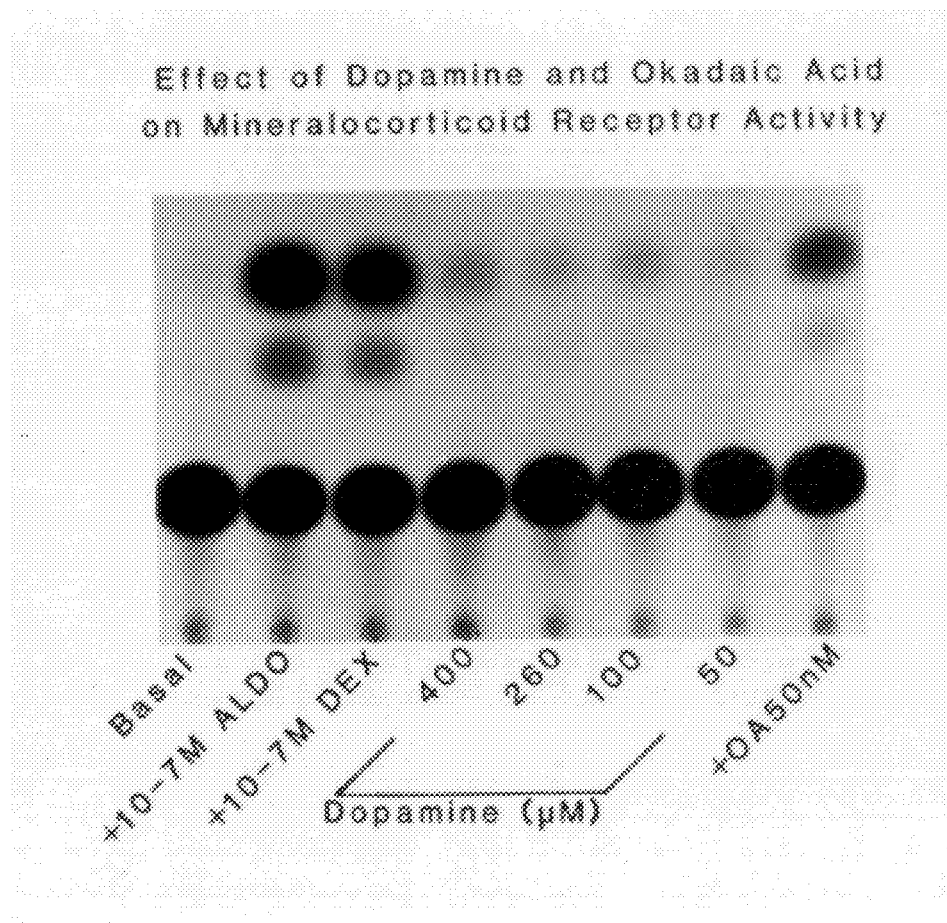
FIG. 6 shows the nuclear receptor activation by dopamine is confined to a subgroup of the steroid/orphan receptor family and that the mineralocorticoid receptor is activated by its cognate ligand, aldosterone, but not significantly activated by dopamine.
Figure 7:
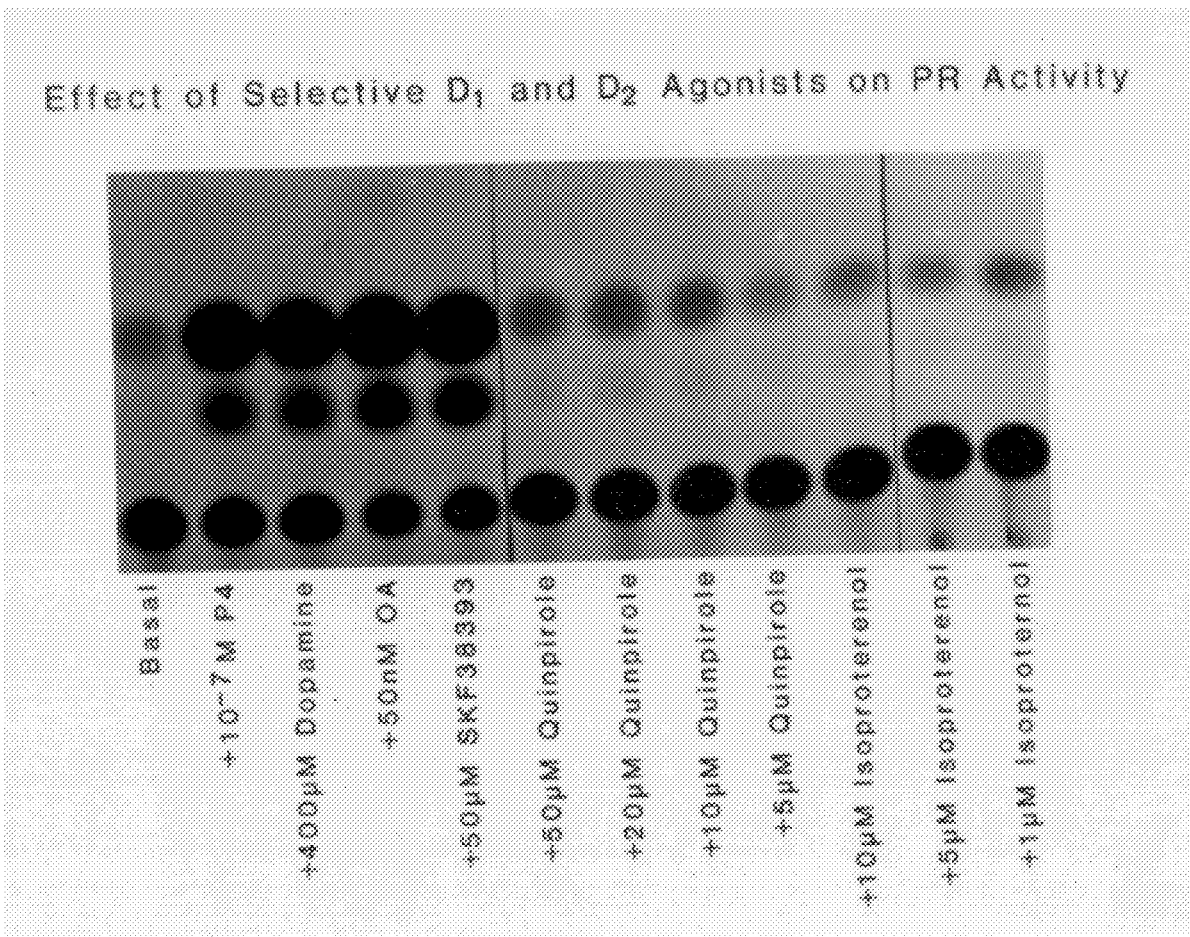
FIG. 7 shows the difference in activation of the indirect pathway of regulation transcription between the $D_1$ and $D_2$ dopamine receptors.

The above assay was also used to look at the effect of dopamine on the steroid/orphan receptor family. (FIGS. 5–6). It was found that the nuclear receptor activation by dopamine is confined to a subgroup of the steroid/orphan receptor family. Additional members glucocorticoid receptor (FIG. 5) and mineralocorticoid receptor (FIG. 6) were activated by their cognate ligands, dexamethasone (DEX) and aldosterone (ALDO) respectively, but are not activated or only marginally activated by dopamine.

EXAMPLE 5

Indirect Activity of Pathway

Since none of the receptors discussed in the previous examples binds dopamine directly, the possibility that the membrane bound $D_1$ or $D_2$ dopamine receptors mediated an indirect pathway of activation of the steroid orphan receptor was examined. In FIG. 6 it was demonstrated that the selective $D_1$ receptor agonist SKF38393 mimicked the dopamine dependent activation of the progesterone receptor while a selective $D_2$ agonist Quinperole or the β adrenergic agonist isoproterenol did not activate the receptor.

EXAMPLE 6

Intracellular Adenylate Cyclase

Figure 8A:
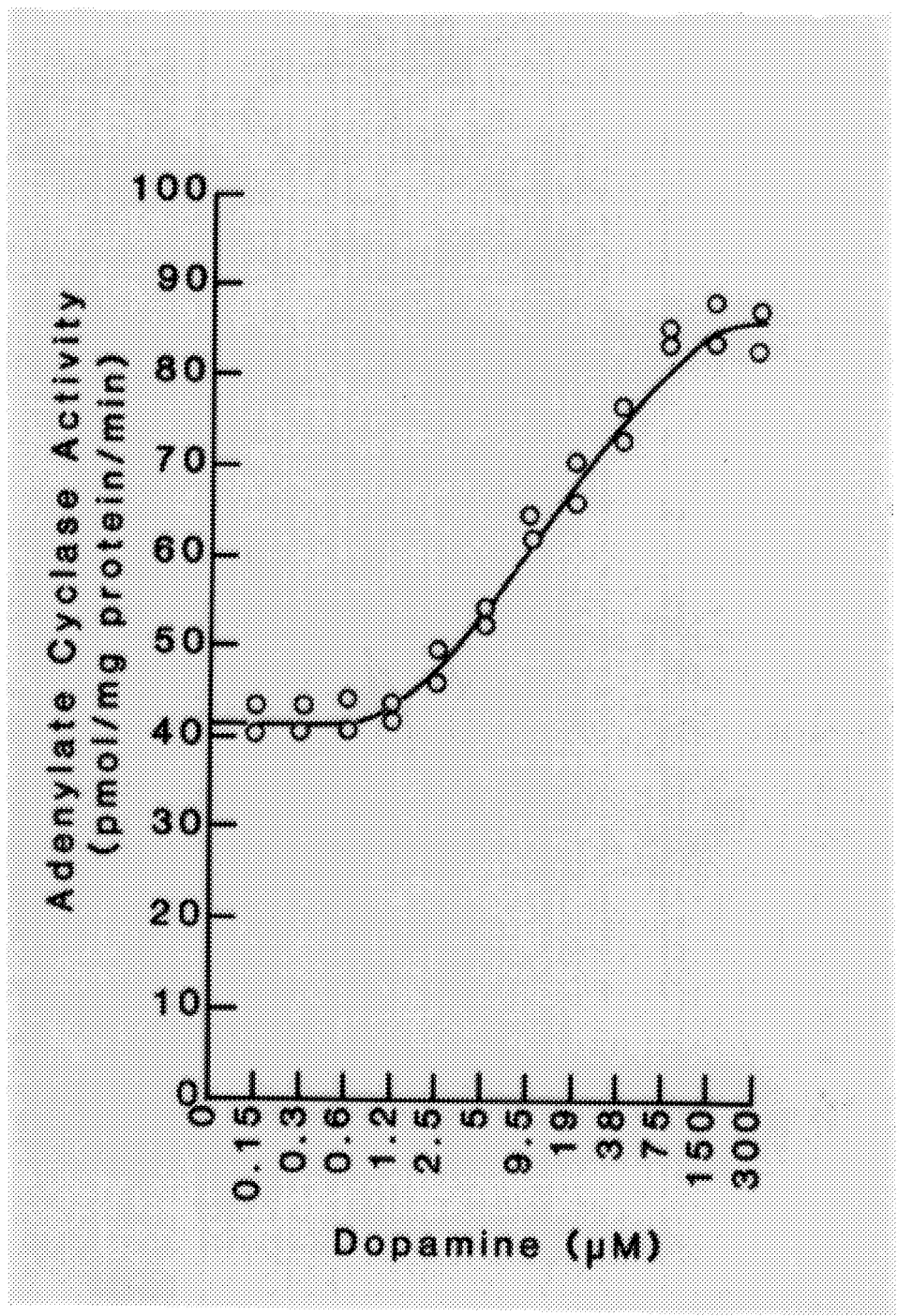
FIG. 8 shows the intercellular levels of adenylate cyclase in CV-1 cells after testing with dopamine and isoproterenol.
Figure 8B:
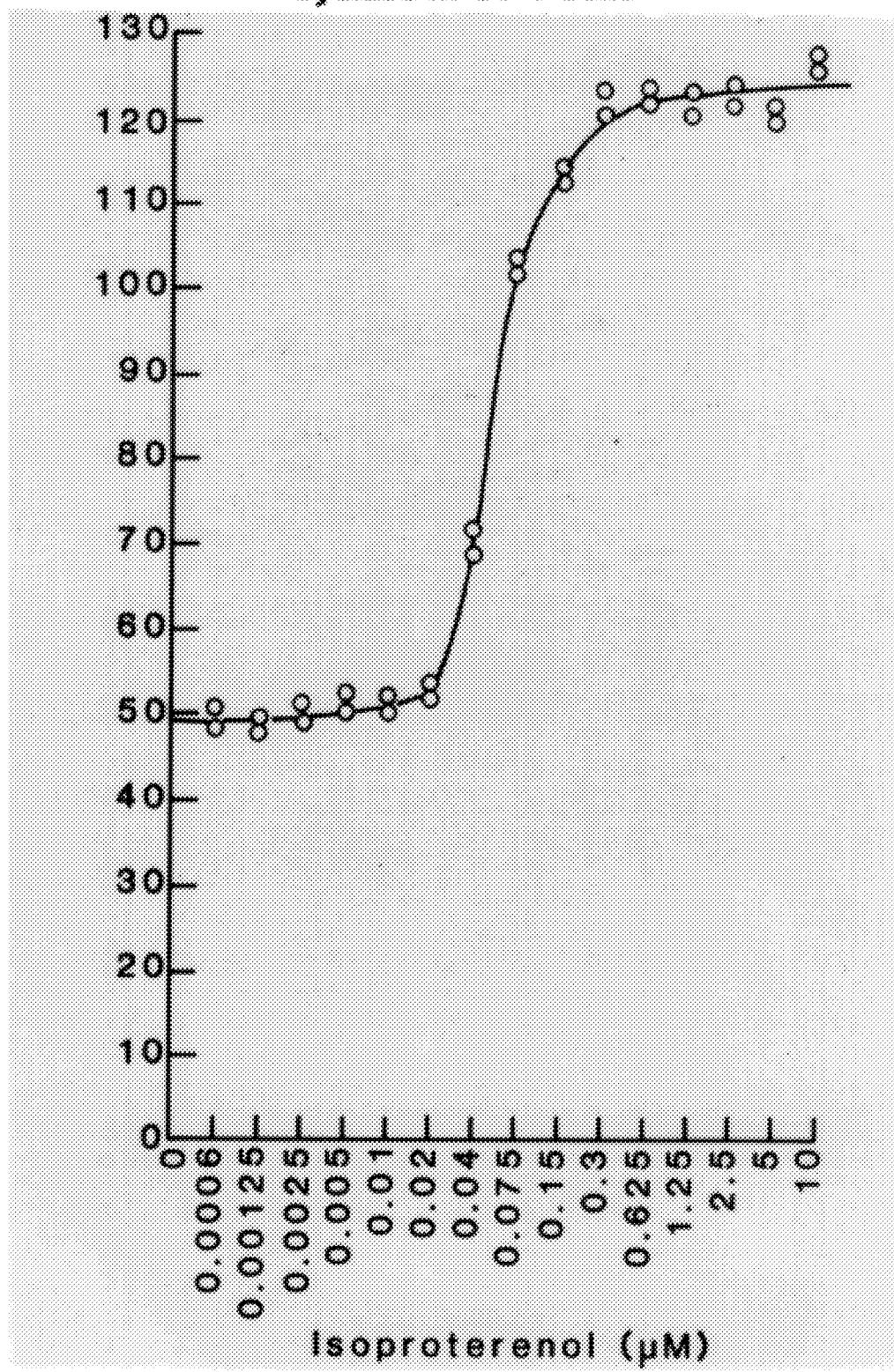

Since $D_1$ and $D_2$ dopamine receptor sites can be distinguished by the ability of $D_1$ sites to activate a intracellular dopamine dependent adenylate cyclase, the intracellular levels of adenylate cyclase in CV-1 cells was measured in response to both dopamine and isoproterenol. (FIG. 8). An increase in intracellular adenylate cyclase levels was found in response to both dopamine and isoproterenol. These data demonstrate that: (1) there is a $D_1$ dopamine receptor in CV-1 cells and (2) this membrane pathway of nuclear receptor activation appears to be selective for dopamine. Isoproterenol which activates a β adrenergic pathway in the cells cannot activate the progesterone receptor.

EXAMPLE 7

COUP-TF Receptor

A chimeric COUP-TF receptor was constructed. This chimeric receptor contained $NH_2$- and COOH-terminal regions of human COUP-TF and the DNA binding domain of the chicken progesterone receptor (cPR) (FIG. 9). PR cDNA was digested with Hind III at nt1801, repaired and ligated to BSM1 digested, blunt ended human COUP-TF cDNA to fuse the PR DNA binding domain to the COOH-terminus of the COUP-TF. A polymerase chain reaction was used to generate a Sac1 site in the COUP-TF cDNA immediately 5' to the DNA binding domain. Sac1 digested COUP-TF cDNA was then ligated to Sac1 digested PR cDNA to fuse the $NH_2$ terminus to COUP-TF to the PR DNA binding domain. The COOH—terminal deletion mutant was made using two in-frame Pst1 sites present in the COUP-TF cDNA. The $PR_A$-COUP chimera was constructed as described above except that the $NH_2$ terminus of PR was left intact. The plasmid adenoviral expression constructs pADCOUP, pADCOUP Δ and pADACOUP were made by inserting the respective chimeric cDNA's into the EcoR1 site of the eukaryotic expression vector P91023(B).

EXAMPLE 8

Induction of CAT Gene Expression

CAT gene expression was induced by dopamine (D), α-ergocryptine (a dopamine receptor agonist, E), 8-bromo-cyclic adenosine monophosphate (8-Br-cAMP) and okadaic acid (OA). As seen in FIG. 4, pADFCOUP (5 ug) and PRETKCAT (5 ug) were co-transfected into CV-1 cells as described herein. Transfection assays were conducted in a PR negative monkey kidney cell line CV-1, transfected with a chimeric COUP construct and a reporter plasmid PRET-KCAT. The reporter contained two copies of a progesterone response element located upstream of the herpes simplex virus thymidine kinase promoter linked to a chloramphenicol acetyl transferase gene. In all experiments, the positions of $^{14}$C-Chloramphenicol and the 1- and 3-acetylated forms of $^{14}$C-Chloramphenicol are indicated (1AC and 3AC, respectively).

Figure 10:
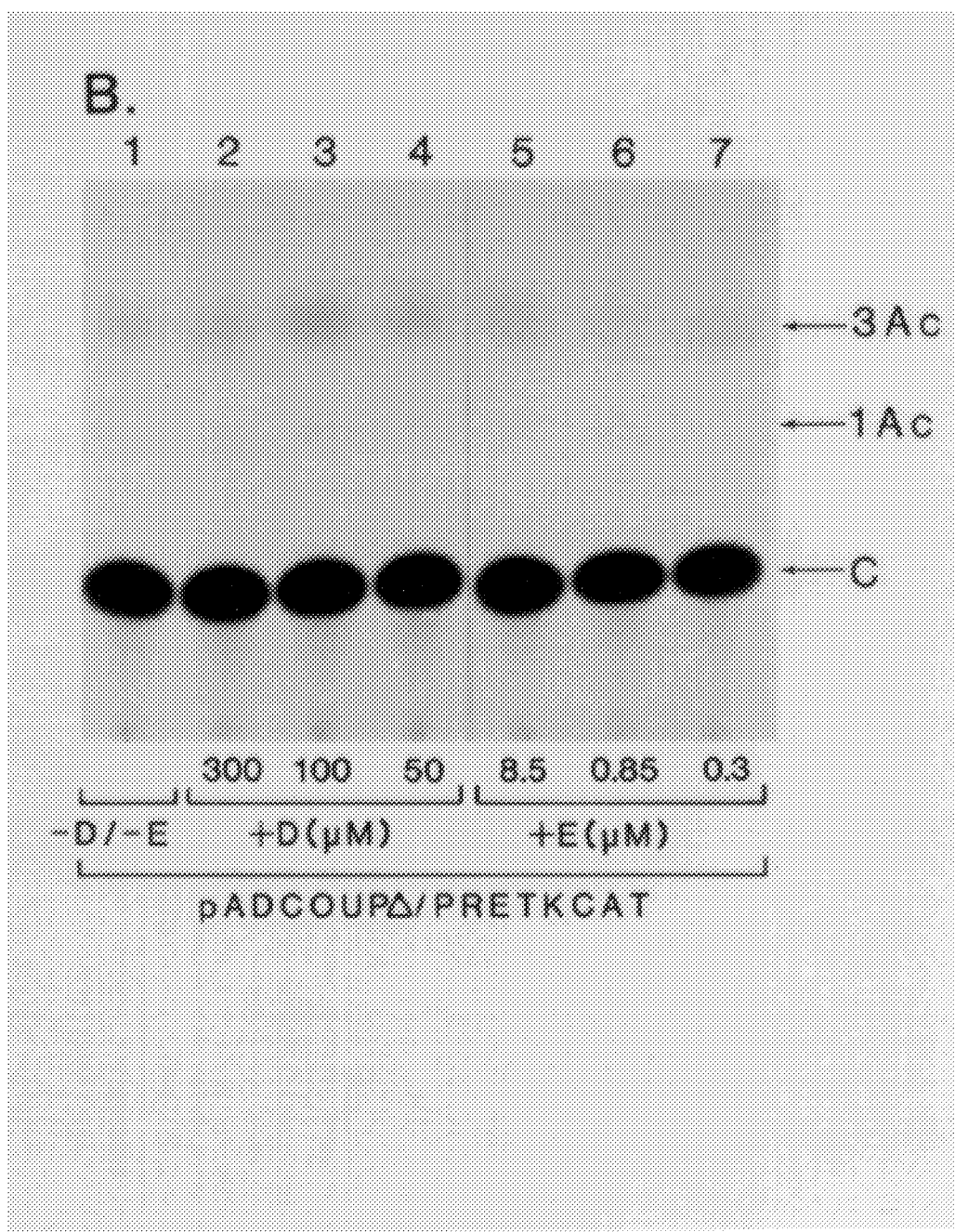
FIG. 10 shows the lack of induction of the chloramphenicol acetyl transferase CAT gene expression in a deficient chimeric COUP-TF gene.

Cells were cultured for two days in serum-free media supplemented with Nutridoma in the absence (lane 1) or presence of varying concentrations of dopamine (lanes 2–7) and α-ergocryptine (lanes 8–11). The media was replaced after 24 hours and fresh compounds were added. As a control, cells were transfected with P91023(B) that lacked COUP-TF coding sequences and PRETKCAT and cultured in the presence of 100 uM dopamine (lane 12). CV-1 cells were prepared for CAT assays as described herein and the assays were performed for 12 hours using 50 ug of protein extract.

pADCOUPΔ (5ug) and PRETKCAT (5 ug) were cotransfected into CV-1 cells cultured as described herein. As seen in FIG. 10, in the absence (lane 1) or presence of varying concentrations of dopamine (lanes-2–4) and α-ergocryptine (lanes 5–7).

Figure 11:
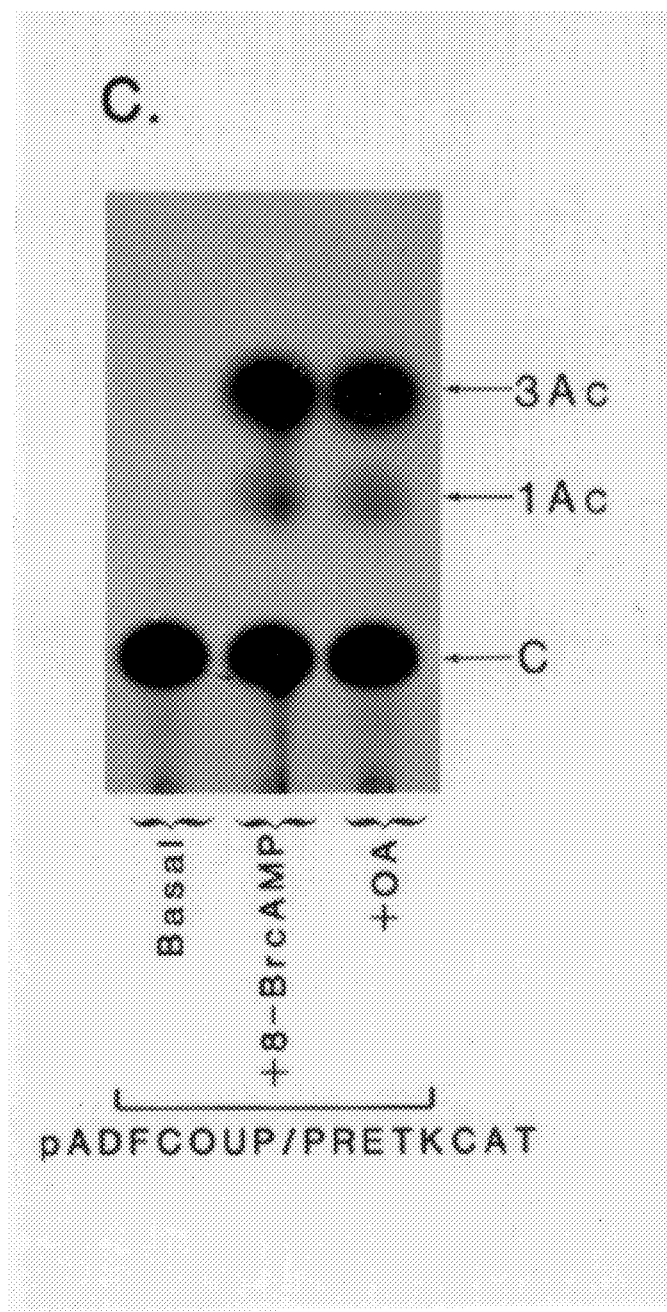
FIG. 11 shows the induction of the CAT gene expression in a chimeric COUP-TF gene.

As seen in FIG. 11, cells were transfected with pADF-COUP (5 ug) and PRETKCAT (5 ug) and were untreated (basal) or treated with $10^{-3}$M 8-Br-cAMP or $5\times10^{-8}$M okadaic acid.

Concentrations of dopamine as low as 3 uM simulated CAT gene activity 5- to 10-fold. Dopamine (100 uM) did not simulate CAT activity in cells transfected with the parent expression vector P91023(B) which lacked COUP-TF coding sequences. This demonstrates that dopamine stimulation of transcription required COUP-TF and did not result from a general increase in transcriptional activity. The dopamine receptor agonist α-ergocryptine also stimulated COUP dependent CAT gene expressions in concentrations as low as 300 nM. Concentrations of α-ergocryptine greater than 8.5 uM inhibited the response. Activation of COUP-TF appears to be relatively specific for dopamine. Further, when a chimeric COUP-TF (COUP DELTA) containing a deletion on the COOH-terminal domain was tested, a stable protein of the correct size was produced but it did not bind to the labelled PRE oligonucleotide. The mutant protein is not capable of transcriptional activation. This argues against the hypothesis that the effect of transcription is brought about by dopamine mediated stimulation of transcription factors unrelated to COUP-TF.

EXAMPLE 9

Non-Binding of Dopamine to COUP-TF

Studies with either $^3$H-dopamine or $^3$H-α-ergocryptine failed to show high affinity binding to human COUP-TF. The COUP-TF was extracted from transfected cells or produced by in vitro translation in rabbit reticulocyte lysate. Thus, dopamine does not bind directly to COUP-TF in the mediation of transcription. Further support of this is that there is no notable homologies between COUP-TF and published dopamine receptor sequences. Thus, it is likely that the activation of COUP-TF by dopamine is a phosphorylation mediated event brought about by dopamine stimulation of cell surface receptors. In this context, it is important that 8-Br-cAMP, a stimulator of cAMP dependent protein kinase A and okadaic acid, and inhibitor of protein phosphotases 1 and 2A also stimulate COUP-TF dependent transcription in the assay system. Neither of these compounds stimulated transcription in cells transfected with p91023(B) lacking the COUP-TF sequences and PRETKCAT.

Results of the cited examples herein demonstrate the ability of neurotransmitters to activate steroid, vitamin, and orphan receptors, they provide direct evidence of cross-talk between two signal transduction pathways that are not usually thought to be linked. Activation of an intracellular receptor by a membrane receptor agonist prompts a closer look at to whether a classical steroid hormone receptors can be activated by compounds other than cognate ligands.

It is evident from the above results that a novel tissue culture screening system to monitor a transcriptional response and novel assays for measuring the transcription response to membrane signals are provided. These are useful (1) for studying transcriptional responses; (2) to identify compounds which regulate biological activity of steroid, vitamin or orphan receptors; (3) to monitor a transcriptional response triggered by a chemical signal interacting with a plasma membrane receptor; and (4) to measure the coupling of activation of membrane receptors with gene expression. Thus, an important new tool is provided for dissecting the mechanism of regulation of transcriptional events, while also allowing for a rapid screening of a large number of compounds for their ability to regulate transcriptional responses and the receptors which modulate transcriptional responses.

All publications and patent applications mentioned in this specification are indicative of the levels of those skilled in the art to which this invention pertains. All publications and patent applications are herein incorporated by reference to the same extent as if each individual publication or patent application was specifically and individually indicated to be incorporated by reference.

One skilled in the art will readily appreciate that the present invention is well adapted to carry out the objects and obtain the ends and advantages mentioned, as well as those inherent therein. The assay system and the methods, procedures and techniques described herein are presently representative of preferred embodiments, are intended to be exemplary and are not intended as limitations on the scope. Changes therein and other uses will occur to those skilled in the art which are encompassed within the spirit of the invention or deemed by the scope of the appended claims.

What is claimed:

1. An assay for identifying a test compound or chemical signal that indirectly activates a specific intracellular receptor via interaction with a cell membrane receptor, comprising the steps of:

growing in appropriate media a tissue culture screening system cell line containing a membrane receptor; a target gene, wherein said target gene is comprised of a known receptor response enhancer DNA element located upstream of a promoter fused to a reporter gene; and a specific intracellular receptor selected from the group consisting of a steroid receptor, a vitamin receptor, an orphan receptor and a chimeric receptor, wherein said chimeric receptor includes a steroid hormone receptor domain;

adding the test compound or chemical signal to the media; and measuring the amount of product produced by the target gene.

2. The assay of claim 1, wherein the test compound or chemical signal is a potential agonist or antagonist of neurotransmitters which regulate cellular target genes.

3. The assay of claim 1, wherein the test compound or chemical signal potentially acts indirectly by membrane receptor binding to regulate a steroid, a vitamin or an orphan receptor pathway of gene activation or repression.

4. The assay of claim 3, wherein the test compound or chemical signal acts through receptors selected from the group consisting of α adrenergic receptor, β adrenergic receptor, cholinergic receptor, muscarinic receptor, nicotinic receptor and serotinergic receptor.

5. The assay of claim 1, wherein the test compound or chemical signal potentially activates a steroid, a vitamin or an orphan receptor dependent gene regulating pathway in the absence of specific steroid, vitamin or orphan ligand.

6. A The assay of claim 1, wherein the test compound or chemical signal is a non-ligand antagonist that interferes with steroid, vitamin or orphan receptor dependent regulated gene activation.

* * * * *